US00PP25496P2

(12) United States Plant Patent
Trees

(10) Patent No.: US PP25,496 P2
(45) Date of Patent: Apr. 28, 2015

(54) ***RUDBECKIA* PLANT NAMED 'BALRUDOSH'**

(50) Latin Name: *Rudbeckia hirta*
Varietal Denomination: Balrudosh

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 181 days.

(21) Appl. No.: 13/986,984

(22) Filed: Jun. 20, 2013

(51) Int. Cl.
*A01H 5/00* (2006.01)

(52) U.S. Cl.
USPC ..... Plt./474

(58) Field of Classification Search
USPC ..... Plt./474
See application file for complete search history.

*Primary Examiner* — Annette Para
(74) *Attorney, Agent, or Firm* — Audrey Charles

(57) ABSTRACT

A new and distinct cultivar of *Rudbeckia* plant named 'Balrudosh', characterized by its double-type inflorescences having ray florets of yellow and gold with central streaks of greyed-purple and disc florets of black and dark greyed-purple, medium green-colored foliage, and moderately vigorous, upright growth habit, is disclosed.

1 Drawing Sheet

Latin name of genus and species of plant claimed: *Rudbeckia hirta.*

Variety denomination: 'Balrudosh'.

BACKGROUND OF THE INVENTION

The present invention relates to a new and distinct cultivar of *Rudbeckia* plant botanically known as *Rudbeckia hirta* and hereinafter referred to by the cultivar name 'Balrudosh'.

The new cultivar originated in a controlled breeding program in Arroyo Grande, Calif. during July 2008. The objective of the breeding program was the development of *Rudbeckia* cultivars that are freely flowering and propagated using cuttings as opposed to traditional division and tissue culture propagation.

The new *Rudbeckia* cultivar was the result of a self-pollination of 'Cherokee Sunset', not patented, characterized by its double-type, golden-yellow and reddish-bronze colored inflorescences, medium green-colored foliage, and vigorous, upright growth habit. The new cultivar was discovered and selected as a single flowering plant within the progeny of the above stated self-pollination during November 2009 in a controlled environment in Arroyo Grande, Calif.

Asexual reproduction of the new cultivar by terminal stem cuttings since November 2009 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balrudosh' as a new and distinct cultivar of *Rudbeckia* plant:

1. Double-type inflorescences having ray florets of yellow and gold with central streaks of greyed-purple and disc florets of black and dark greyed-purple;
2. Medium green-colored foliage; and
3. Moderately vigorous, upright growth habit.

Of the many commercially available *Rudbeckia* cultivars, the most similar in comparison to the new cultivar is the parent cultivar 'Cherokee Sunset', not patented. However, in comparison, plants of the new cultivar differ from plants of 'Cherokee Sunset' in at least the following characteristics:

1. Plants of the new cultivar have a ray floret color pattern that is different from 'Cherokee Sunset'; and
2. Plants of the new cultivar produce vegetative nodal cuttings unlike 'Cherokee Sunset'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balrudosh'. The plants were grown in 6-inch pots for 8 weeks in a greenhouse in West Chicago, Ill. Plants were pinched 3 weeks before transplant.

DETAILED BOTANICAL DESCRIPTION

Figure 1:
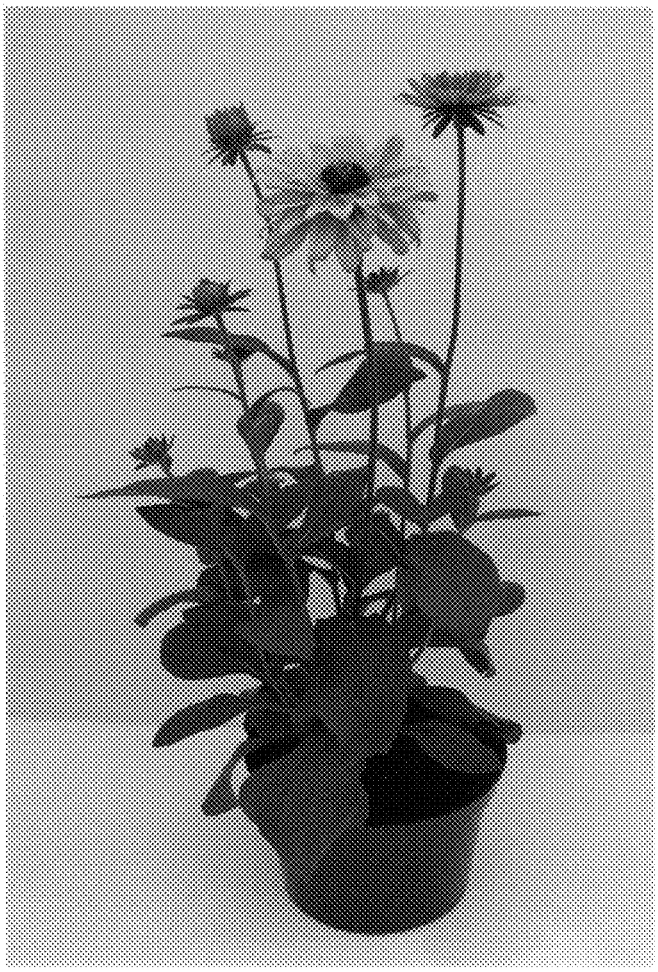
FIG. 1 illustrates a side view of the overall growth and flowering habit of 'Balrudosh'.
Figure 2:
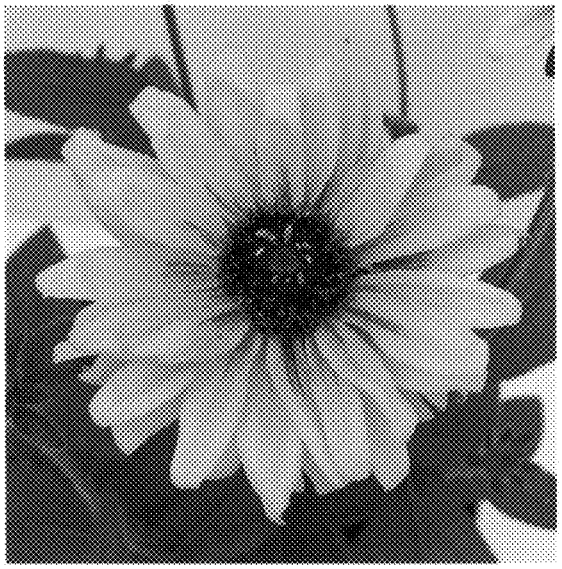
FIG. 2 illustrates a close-up view of an individual inflorescence of 'Balrudosh'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2013 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 6-inch pots for 8 weeks utilizing a soilless growth medium. Plants were pinched 3 weeks before transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Rudbeckia hirta* cultivar Balrudosh.

Parentage:

*Female and male parent*.—'Cherokee Sunset', not patented.

Propagation:

*Type cutting*.—Vegetative nodal cuttings.

*Time to initiate roots*.—Approximately 7 to 10 days.

*Time to produce a rooted cutting*.—Approximately 5 to 6 weeks.

*Root description*.—Fibrous.

*Rooting habit*.—Freely branching.

Plant description:

*Commercial crop time*.—Approximately 8 to 10 weeks from a rooted cutting to finish in a 15 cm pot.

*Growth habit and general appearance*.—Moderately vigorous, upright.

*Size*.—Height from soil level to top of plant plane: Approximately 44.0 cm. Width: Approximately 31.2 cm.

*Branching habit*.—Freely branching, pinching improves basal branching. Quantity of main branches per plant: Approximately 7.

*Branch*.—Strength: Strong. Length: Approximately 29.5 cm. Diameter: Approximately 4.0 mm. Length of central internode: Approximately 6.0 cm. Texture: Moderate hispid pubescence. Color of young stem: 144B. Color of mature stem: 146A.

Foliage description:

*General description*.—Quantity of leaves per main branch: Approximately 6. Fragrance: None detected. Form: Simple. Arrangement: Alternate.

*Leaves*.—Aspect: Perpendicular to stem with tip downward turning. Shape: Obovate to elliptic. Margin: Serrate. Apex: Acute. Base: Sessile. Venation pattern: Pinnate. Length of mature leaf: Approximately 13.2 cm. Width of mature leaf: 5.3 cm. Texture of upper and lower surfaces: Moderate hispid pubescence. Color of upper surface of young foliage: Closest to N137A with venation of 145A. Color of lower surface of young foliage: 137B with venation of 147C. Color of upper surface of mature foliage: Closest to N137A with venation of 145C. Color of lower surface of mature foliage: Closest to 147B with venation of 147C.

Flowering description:

*Flowering habit*.—'Balrudosh' is freely flowering under outdoor growing conditions with substantially continuous blooming from spring through autumn and year-round in greenhouse environment.

*Lastingness of individual inflorescence on the plant*.—Approximately 2 weeks.

Inflorescence description:

*General description*.—Type: Solitary, double, composite. Persistent. Shape: Round. Aspect: Facing upward and outward. Arrangement: Positioned above foliage, borne on terminal and axillary peduncles. Quantity per plant: Approximately 2. Diameter: Approximately 8.0 cm. Depth: Approximately 5.0 cm. Fragrance: None detected.

*Peduncle*.—Strength: Strong. Aspect: Erect to acute angle from stem. Length: Approximately 26.5 cm. Diameter: Approximately 3.0 mm. Texture: Longitudinally ribbed, moderate hispid pubescence. Color: 146A.

*Bud*.—Rate of opening: Generally takes 2 to 3 weeks for bud to progress from first color to fully open flower. Quantity per plant: Approximately 5.

*Bud just before opening*.—Shape: Globular. Diameter: Approximately 1.6 cm. Color: 145A.

*Ray florets*.—Quantity per inflorescence: Approximately 70. Arrangement: In multiple whorls. Aspect: Initially erect, becoming reflexed with age. Shape: Elliptic. Margin: Entire. Apex: Emarginate to preamorse. Base: Attenuate. Length of outer whorl: Approximately 4.0 cm. Width of outer whorl: Approximately 1.5 cm. Length of inner whorl: Approximately 7.0 mm. Width of inner whorl: Approximately 3.0 mm. Texture of upper surface: Glabrous, two longitudinal ribs. Texture of lower surface: Two longitudinal ribs, moderate strigose pubescence. Pubescence color: 187A. Color of upper surface when first open: 15A with lower half of 21A. Color of lower surface when first open: 15C. Color of upper surface when fully open: Upper third of 14A, lower two thirds of 21A with central streaks of 187C. Color of lower surface when fully open: 15B with ribs of 144A.

*Disc florets*.—Quantity per inflorescence: Approximately 250 to 300. Arrangement: Massed at center of receptacle. Shape: Tubular. Margin: Entire. Apex: Five acute tips. Base: Fused. Length: Approximately 8.0 mm. Diameter at apex: Approximately 1.0 mm. Diameter at base: Approximately 1.0 mm. Texture: Glabrous. Color when first open: 203C transitioning through 187A to base of NN155B. Color when fully open: 203C transitioning through 187A to base of 203C.

*Disc*.—Diameter: Approximately 1.7 cm. Depth: Approximately 1.3 cm.

*Receptacle*.—Shape: Broadly conical. Height: Approximately 5.0 mm. Diameter at base: Approximately 9.0 mm. Color: 145D.

*Phyllaries*.—Quantity per inflorescence Approximately 30. Arrangement: In two whorls. Shape: Outer whorl narrow ovate, inner whorl lancelolate. Margin: Entire. Apex: Acute. Base: Truncate. Length: Approximately 2.4 cm. Width: Approximately 8.0 mm. Texture of upper and lower surfaces: Moderate hispid pubescence. Color of upper surface: N137A. Color of lower surface: 137B.

*Reproductive organs*.—Androecium: Present on disc florets only. Stamen quantity: 5. Stamen length: Approximately 5.0 mm. Anther shape: Oblong. Anther length: Approximately 3.0 mm. Anther color: 203C. Pollen amount: Moderate. Pollen color: 12A. Gynoecium: Present on ray and disc florets. Pistil quantity: 1 per floret. Pistil length: Approximately 8.0 mm. Stigma shape: two-parted, feather-like. Stigma length: Approximately 2.0 mm. Stigma color: 203C.

Style length: Approximately 4.0 mm. Style color: 203C transitioning through 187A to base of NN155B.

Ovary length: Approximately 2.0 mm. Ovary color: 155D maturing to 203C.

Seed and fruit production: Neither seed nor fruit production has been observed.

Disease and pest resistance: Resistance to pathogens and pests common to *Rudbeckia* has not been observed.

What is claimed is:

1. A new and distinct cultivar of *Rudbeckia* plant named 'Balrudosh', substantially as herein shown and described.

* * * * *